US011053186B2

(12) United States Patent
Roberts et al.

(10) Patent No.: US 11,053,186 B2
(45) Date of Patent: *Jul. 6, 2021

(54) PROCESS FOR THE PRODUCTION OF GLYCOLIC ACID

(71) Applicant: Johnson Matthey Davy Technologies Limited, London (GB)

(72) Inventors: Dena Roberts, Durham (GB); David John Watson, London (GB); John Swinney, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/839,971

(22) Filed: Apr. 3, 2020

(65) Prior Publication Data

US 2020/0239395 A1  Jul. 30, 2020

Related U.S. Application Data

(63) Continuation of application No. 16/332,853, filed as application No. PCT/GB2017/052740 on Sep. 15, 2017, now Pat. No. 10,640,443.

(30) Foreign Application Priority Data

Sep. 16, 2016  (GB) ..................... 1615762

(51) Int. Cl.
    *C07C 51/12* (2006.01)
    *C07C 67/08* (2006.01)
    *C07C 67/54* (2006.01)
    *C07C 51/09* (2006.01)
    *C07C 59/06* (2006.01)
    *C07C 69/675* (2006.01)

(52) U.S. Cl.
    CPC ............. *C07C 51/12* (2013.01); *C07C 51/09* (2013.01); *C07C 59/06* (2013.01); *C07C 67/08* (2013.01); *C07C 67/54* (2013.01); *C07C 69/675* (2013.01); *Y02P 20/10* (2015.11)

(58) Field of Classification Search
    CPC ......... C07C 51/12; C07C 51/09; C07C 59/06; C07C 67/54
    See application file for complete search history.

(56) References Cited

U.S. PATENT DOCUMENTS

| 2,152,852 A | * | 4/1939 | Loder | C07C 51/12 562/518 |
| 2,285,444 A | * | 6/1942 | Kloid | B41J 5/38 400/180 |
| 2,443,482 A | * | 6/1948 | Shattuck | C07C 51/12 562/518 |
| 3,859,349 A | * | 1/1975 | Cody | C07C 51/42 562/580 |
| 3,911,003 A | * | 10/1975 | Suzuki | C07C 51/12 562/518 |
| 4,016,208 A | * | 4/1977 | Suzuki | C07C 51/12 562/518 |
| 4,052,452 A | * | 10/1977 | Scardigno | C07C 51/12 562/518 |
| 4,087,470 A | * | 5/1978 | Suzuki | C07C 29/149 568/864 |
| 4,136,112 A | * | 1/1979 | Bakshi | C07C 51/10 562/518 |
| 4,140,866 A | * | 2/1979 | Nielsen | C07C 29/149 560/189 |
| 4,188,494 A | * | 2/1980 | Suzuki | C07C 51/42 560/179 |
| 4,431,486 A | * | 2/1984 | Balmat | C07C 51/12 203/69 |
| 4,431,997 A | | 2/1984 | Sasser et al. | |

(Continued)

FOREIGN PATENT DOCUMENTS

| CN | 103833548 A | 6/2014 |
| DE | 3133353 A1 | 3/1983 |
| EP | 0114657 A1 | 8/1984 |

(Continued)

OTHER PUBLICATIONS

He et al., Catalysis Today, 51 (Jun. 1, 1999), 127-134.
Pan et al., Studies in Surface Science and Catalysis, vol. 88, 1994. pp. 223-231.
Japanese Notice of Reasons for Rejection for JP2019-514823 dated Apr. 20, 2021, English Translation.

*Primary Examiner* — Sikarl A Witherspoon
(74) *Attorney, Agent, or Firm* — BakerHostetler

(57) ABSTRACT

A process for the production of glycolic acid or a derivative thereof comprises: reacting formaldehyde with carbon monoxide and water in a carbonylation reactor in the presence of a sulfur catalyst, said reactor operating under suitable conditions, such that glycolic acid is formed; recovering a first product stream comprising glycolic acid, impurities and a sulfur species in the carbonylation reactor; passing the first product stream to an esterification reactor where it is subjected to esterification to form an alkylglycolate and wherein the esterification is catalysed by the sulfur species recovered in the first product stream; recovering a second product stream comprising the alkylglycolate, sulfur species and impurities from the esterification reactor; separating the sulfur species from the second product stream and recycling it to the carbonylation reactor in step (a) to form a sulphur depleted second product stream; separating the alkylglycolate from the sulphur depleted second product stream in a distillation zone; and recovering the alkylglycolate and converting the alkylglycolate to glycolic acid.

26 Claims, 2 Drawing Sheets

(56) References Cited

U.S. PATENT DOCUMENTS

| | | | |
|---|---|---|---|
| 4,824,997 A * | 4/1989 | MacFarlane | C07C 69/675 |
| | | | 560/179 |
| 5,688,288 A | 11/1997 | Yoshiki et al. | |
| 6,376,723 B2 * | 4/2002 | Drent | C07C 29/149 |
| | | | 560/129 |
| 2004/0138409 A1 * | 7/2004 | Hayashi | C07C 67/40 |
| | | | 528/354 |
| 2010/0290962 A1 | 11/2010 | Wilson et al. | |
| 2013/0261328 A1 | 10/2013 | Barnicki et al. | |
| 2013/0331605 A1 | 12/2013 | Janka et al. | |

FOREIGN PATENT DOCUMENTS

| | | |
|---|---|---|
| EP | 1360222 A1 | 11/2003 |
| EP | 1786850 A1 | 5/2007 |
| GB | 1499245 A | 1/1978 |
| GB | 1595231 A | 8/1981 |
| GB | 2542869 A | 4/2017 |
| JP | 56073042 A2 | 6/1981 |
| JP | S60-260538 A | 12/1985 |
| JP | S60260538 A | 12/1985 |
| JP | H01246243 A | 10/1989 |
| JP | H11-335319 A | 12/1999 |
| JP | 2004043386 A | 2/2004 |
| JP | 2005247694 A | 9/2005 |
| JP | 2503178 B2 | 4/2017 |
| KR | 19950011114 B1 | 9/1995 |
| KR | 19950013078 B1 | 10/1995 |
| KR | 0124821 B1 | 12/1997 |
| KR | 0155273 B1 | 10/1998 |
| KR | 100356768 B1 | 9/2003 |
| WO | 2006013080 A1 | 2/2006 |
| WO | 2007090676 A1 | 8/2007 |
| WO | 2009140787 A1 | 11/2009 |
| WO | 2009140850 A1 | 11/2009 |
| WO | 2013148497 A1 | 10/2013 |
| WO | 2016162662 A1 | 10/2016 |
| WO | 2016162663 A1 | 10/2016 |

* cited by examiner

PROCESS FOR THE PRODUCTION OF GLYCOLIC ACID

CROSS-REFERENCE TO RELATED APPLICATIONS

This application is a continuation of U.S. Ser. No. 16/332,853, filed Mar. 13, 2019, which is the National Stage of International Patent Application No. PCT/GB2017/052740, filed Sep. 15, 2017, which claims priority from Great Britain Patent Application No. 1615762.0, filed Sep. 16, 2016, the disclosures of each of which applications are incorporated herein by reference in their entireties for any and all purposes.

FIELD

The present invention relates to a process for the production of a hydroxy acid, more particularly glycolic acid, or derivatives thereof. More particularly, the present invention relates to a process for the production of a hydroxy acid, such as glycolic acid, or derivatives thereof having a purity which is at least about 70%.

BACKGROUND

The reaction to form glycolic acid by the carbonylation of formaldehyde with carbon monoxide using strong acid catalysts is well known. The basic process was first disclosed by DuPont in U.S. Pat. No. 2,152,852. The process was for the preparation of glycolic acid in the liquid phase by reacting formaldehyde, water and carbon monoxide in the presence of a homogeneous acid catalyst at temperatures between 50 and 350° C. and at a pressure between 5 and 1500 atma. Sulphuric acid, hydrochloric acid, phosphoric acid, boron fluoride, formic acid and glycolic acid are described as suitable catalysts.

DuPont went on to obtain further patents for the production of glycolic acid such as U.S. Pat. No. 2,285,444 which discloses a continuous process for the hydrogenation of glycolic acid to ethylene glycol and U.S. Pat. No. 2,443,482 which discloses a continuous process for formaldehyde carbonylation.

The process for producing ethylene glycol was commercialized and operated by DuPont until the late 1960's when this route to ethylene glycol became uncompetitive. The plant was then operated for the production of glycolic acid in which sulphuric acid was used as catalyst at a temperature of 200° C. and at a pressure of from 400 to 700 bar.

The processes described in these initial early cases suffered from numerous problems. These problems included those attributable to the need to work at very high pressure. In addition, the selectivity was poor. It was also necessary to contend with the highly corrosive reaction mixture and the difficulty of removing the homogeneous acid catalyst such as sulphuric acid from the reaction product.

Various proposals have been made to address some or all of these problems. For example, in U.S. Pat. No. 3,859,349 there is a proposal to address the problems associated with separating the sulphuric acid catalyst and suggests using ion exchange resins as an alternative to neutralisation with calcium carbonate, which had been the previous approach. However, the ion exchange resins have limited thermal stability in aqueous environments leading to the loss of acid groups.

Another proposal was that described in U.S. Pat. No. 4,431,486 in which azeotropic distillation of crude glycolic acid was proposed as a means of reducing the water content in the recycle to the carbonylation reactors thereby minimising byproduct formation and increasing the yield from the feed formaldehyde.

Another approach has been to look at alternative catalyst systems as a means of reducing reactor operating pressure. Hydrogen fluoride has been suggested as being a suitable catalyst in U.S. Pat. Nos. 3,911,003, 4,016,208, 4,087,470, 4,136,112 and 4,188,494. Processes which use hydrogen fluoride in place of sulphuric acid as catalyst are suggested to allow operating pressures of 1 to 275 bar.

A further alternative process is disclosed in U.S. Pat. No. 4,052,452 in which Cu(I) or Ag salts in concentrated sulfuric acid are suggested as a means of increasing the carbon monoxide solubility and it is suggested that this enables the operating pressure to be reduced to between 0.1 and 30 atma. Whilst this may address the operating pressure issues, such systems are extremely sensitive to poisoning by water and separation and recycle of the metallic catalyst is difficult.

GB1595231 describes a process for the reaction of formaldehyde or one of its linear or cyclic polymers with carbon monoxide in the presence of an alcohol to obtain a glycolic acid using a sulphonic acid catalyst. However a problem with in situ esterification is that the system is inefficient since there is excessive by-product formation. For example where the alcohol is methanol, methoxyacetic acid is formed.

A further in situ process is described in US2013/261328 in which carbon monoxide, aqueous formaldehyde, a homogeneous acid catalyst and a carboxylic acid comprising 3 to 6 carbon atoms is used. Again the presence of the carboxylic acid can lead to the problems with by-product formation.

In U.S. Pat. No. 6,376,723 it is proposed that the reaction should be conducted with an acid catalyst having a pKa value of less than −1 in the presence of a sulphone as a means of moderating the reaction conditions. There is also a suggestion that heterogeneous catalysts could be used.

U.S. Pat. No. 4,140,866 looks at the problems associated with removing the sulfuric acid catalyst from glycolic acid produced by formaldehyde carbonylation. The proposed solution is to first treat the reaction mixture with an alkali metal hydroxide to form the dissolved sulfate salt and this is then precipitated on esterification of the glycolic acid with ethylene dioxide and removal of water.

A widely adopted strategy for overcoming the problems associated with separating homogeneous catalysts from reaction mixtures is to replace the homogeneous catalysts with heterogeneous catalysts that can easily be mechanically separated. Several solid acid materials have been suggested as suitable catalysts for use in formaldehyde carbonylation reactions. These include sulfonic acid ion exchange resins, aluminosilicate zeolites, polyoxometalate salts and alkyl sulfonic acid polysiloxanes.

The use of solid insoluble particulate acidic catalysts having a hydrogen ion exchange capacity in excess of 0.1 milliequivalents per gram was first described in GB1499245. Sulfonic acid based ion exchange resins, acid clays and zeolites are listed as suitable catalysts for formaldehyde carbonylation. These include sulfonic acid ion exchange resins, aluminosilicate zeolites, polyoxometalate salts and alkyl sulfonic acid polysiloxanes.

The use of solid insoluble particulate acidic catalysts having a hydrogen ion exchange capacity in excess of 0.1 milliequivalents per gram was first described in GB1499245. Sulfonic acid based ion-exchange resins, acid clays and zeolites are listed as suitable catalysts. Strongly acidic cation exchange resins in a reaction solvent such as acetic acid are suggested in JP56073042A2 and the use of FZ-1 and ZSM type zeolites in EP0114657.

An alternative process for the preparation of glycolic acid or its esters is disclosed in DE3133353C2. In this process, formaldehyde is reacted with carbon monoxide and water or an alcohol in an inert diluent in two reaction steps. In the first step, formaldehyde is reacted with carbon monoxide using an acidic, solid, insoluble, finely distributed catalyst at a ratio of hydrogen ion exchange capacity of the catalyst to the molar amount of the formaldehyde of 1:1 to 5:1, a temperature of 30° C. to 200° C. and a pressure of 10 to 325 bar. In the second step, water or an alcohol having 1 to 20 carbon atoms is added at a temperature of 20° C. to 200° C. and a pressure of 1 to 325 bar. The catalyst is subsequently mechanically separated from the reaction medium.

KR19950013078B1 relates to a process for producing glycolic acid in which formaldehyde and carbon monoxide are reacted in the presence of water or water-methanol mixture using a heterogeneous solid catalyst, which is polymeric strong acid catalyst ion-exchanged by 5-40 wt % with monovalent metal of Group IB in a water-soluble inert solvent. Dioxane is used as a water-soluble inert solvent.

A similar process is described in KR19950013079B1 in which formaldehyde and carbon monoxide are reacted in the presence of water or water-methanol mixture using a polymeric strong acid catalyst in a water-soluble inert solvent.

A process for continuously manufacturing methyl glycolate from formaldehyde, carbon oxide and methanol is described in KR19950009480B1 in which a flow reactor filled with a polymeric strong acid catalyst is used. Reactant mixture of formaldehyde, water and inert solvent and carbon monoxide is supplied to the upper part of the reactor, and methanol is supplied to the lower part. In the upper part of the reactor, glycolic acid is produced via acid catalysis. In the lower part of the reactor, methyl glycolate is prepared from methanol and formed glycolic acid. The pressure of carbon monoxide is 500 to 6,000 psig and the temperature is 80 to 200° C. The suggested selectivity for this one-step procedure is relatively high.

KR0124821B1 relates to separating methylglycolate from an acidic solution. In this case, the reaction solution formed by a carbonylation reaction and an esterification reaction contains methyl glycolate, dioxane, water, methanol and hydrogen ion. This reaction solution is sent to a neutralization reactor and is neutralized by the addition of alkali to give a salt. The reaction solution containing salt is distilled to separate methanol, water and dioxane from methyl glycolate, salt and dioxane. The methanol separated from dioxane is recirculated to the carbonylation reactor. The solution which separated from the lower part of the distillation tower contains methyl glycolate, salt and dioxane. This is sent to a solid-liquid separator to separate the methyl glycolate from the solvent.

A further process for the production of methyl glycolate is described in KR19950011114B1. In this process formaldehyde is reacted with carbon monoxide to make a glycolic acid. The glycolic acid is then reacted with methanol to make a methyl glycolate. Residual formaldehyde is then reacted with methanol to make methylal. The methyl glycolate and methylal are then separated by distillation. The methylal is reacted with a Fe—Mo catalyst to return it to formaldehyde which is then recovered and concentrated before being recycled.

An alternative heterogeneous acid catalyst for the formaldehyde carbonylation reaction is described in U.S. Pat. No. 6,376,723. Sulfonic acid based ion exchange resins such as Amberlyst 38W and Nafion SAC13 are mentioned as suitable commercially available catalysts. Deloxan ASP 1/9, an alkyl sulfonic acid polysiloxane, is also listed as a suitable catalyst. This material is formed by co-polycondensation of propyl(3-sulfonic acid)siloxane and $SiO_2$.

He et al., Catalysis Today, 51 (1999), 127-134, discloses the use of heteropolyacids as homogeneous catalysts for the condensation of formaldehyde and methyl formate.

A further process is disclosed in JP2503178. In this process, glycolic acid is formed by hydrolysis of polyglycolide made from formaldehyde and carbon monoxide in the presence of a solid heteropoly acid.

WO2009/140787, WO2009/140788 and WO2009/140850 relate to processes using insoluble polyoxometalate compounds. These compounds either have specific acid properties or are encapsulated within zeolite cages, as solid acid catalysts, to produce glycolic acid from carbon monoxide and formaldehyde. However, the metal salts are prone to leaching of the metal component, which will reduce the number of active acid sites. In the case of zeolite impregnated with polyoxometalate salts, acid leaching will impact both the zeolite substrate and the salts themselves.

There are also a number of cases relating to various substituted organopolysiloxane compounds and their uses. These cases can be grouped into five families which cover different classes of polysiloxane compounds. The five groupings can be typified by: EP1360222, EP1786850, WO2006/013080, WO2007/090676 and US2010/0290962 which disclose various families of compounds. These documents suggest that the compounds may be useful for carbonylation reactions, but there is no detailed teaching as to how these compounds may be used in carbonylation reactions in general nor whether or how they may be used in carbonylation of formaldehyde.

It has been suggested that the use of heterogeneous catalysts will reduce the corrosion of the reaction system. None of the heterogeneous catalysts proposed in the prior art has been adopted commercially.

Although there have been numerous patents and publications relating to the production of ethylene glycol from glycolic acid which is formed by carbonylation of formaldehyde, there remains a need for an improved process which can compete economically with the established industrial production route.

The various approaches to trying to solve the problems associated with the reaction can be summarized into two categories. The first relates to the investigation of homogeneous catalyst systems which operate at lower pressure and lower acid concentration than has previously been achievable.

The second relates to the investigation of heterogeneous solid acid catalysts as these benefit from easier separation of the catalyst and reduced reactor corrosion. However, the solid catalysts proposed to date have also proved to have a number of shortcomings and have not been adopted commercially. These catalysts generally lack the thermal and chemical stability required to withstand the severe reaction conditions.

For example, aluminosilicate zeolites are not stable under highly acidic conditions, as the aluminium is leached from the structure causing it to collapse. This results in loss of activity and eventually complete disintegration of the catalyst (Pan et al, 1994, Studies in Surface Science and Catalysis). With a view to avoid this problem, it is proposed in EP0114657 that the reaction should be operated such that the amount of acid formed is limited, but this reduces the efficiency of the reactor and exacerbates separation problems.

It is well known that sulfonic acid based ion exchange resins have limited thermal stability in aqueous environments leading to a loss of acid groups. Furthermore it has been found that formaldehyde attacks the aromatic rings within styrene/di vinyl benzene based resins causing swelling and further loss of acid groups.

It has been shown that substituted organopolysiloxane compounds, such as Deloxan ASP 1/9, QuadraSil—SA and Silicycle (SCX-2), and alkyl sulfonic acid polysiloxanes, can be used but these have been found to quickly lose catalytic performance at effective process conditions. This has been attributed to the loss of the tethered organic acid groups due to hydrolysis.

There therefore remains a need to provide a process for the production of glycolic acid which is economically viable.

In investigating the problem of solid acid catalyst stability in the formaldehyde carbonylation environment a large number of materials have been tested. In the course of this testing, it was observed that the initial activity of a functionalized catalytic silica material reduced with time. By 'functionalized', we mean that the silica material has acid groups, for example, alkyl sulfonic acid groups, tethered to the silica support. It has been discovered that the reduction in activity is a function of removal of the tethered functionalized groups.

An alternative catalyst and a process for the carbonylation of an aldehyde to form a carboxylic acid or derivate thereof is described in WO2016/162663. The catalyst disclosed therein comprises a homogeneous acid catalyst component and a porous solid component.

An alternative improved process for the production of glycolic acid is described in WO 2016/162662. This process relates to the discovery that when the reaction is carried out in the presence of a small quantity of an homogeneous alkyl silyl sulfonic acid, that the reduction in activity of the silica material can be recovered or avoided. In some situations an enhanced activity can be achieved. Thus WO 2016/162662 relates to a process for the production of glycolic acid or derivatives thereof from formaldehyde comprising reacting formaldehyde with carbon monoxide and water in the presence of a silica catalyst, wherein from about 200 to about 1000 ppm of an alkyl silyl sulfonic acid is supplied to the reaction.

Whatever process is used for the production of acids such as glycolic acid, impurities are introduced into the final product. For example, glycolic acid obtained by the carbonylation of formaldehyde in water, in the presence of an acid catalyst, contains glycolic acid dimers and/or oligomers formed by ester-forming dehydrocondensation of glycolic acid. Diglycolic acid may also be present. In addition, catalyst residues will generally be present.

Separation of the desired glycolic acid from these impurities is difficult since the acid is non-volatile and cannot be easily distilled, even under reduced pressure. It is also undesirable to heat the glycolic acid since at higher temperatures, a self-esterification reaction may occur resulting in the formation of polyglycolide and water.

Conventionally, any polyacids formed may be removed by hydrolysis achieved by dilution of 70% glycolic acid with water to about 20% or less and refluxing. This rate of hydrolysis may be improved by the addition of alkali. Whilst this dilution procedure can be used to convert the glycolic acid dimer to the monomer, there will still be other impurities present.

There therefore remains a need to provide a process for the production of glycolic acid or derivatives thereof with improved purity that is economically viable and that preferably can be used in a commercial environment on a large scale. The process will also be suitable for the production of other acids by carbonylation reactions or derivatives thereof and will address corresponding problems associated with these reactions.

SUMMARY

As discussed in WO2016/162662, some classes of acidic polysiloxanes used as catalysts for the hydroxycarbonylation reaction are unstable towards functional group loss. The species liberated from the surface of the catalyst is a sulfonic acid with the trihydroxysilyl group attached to the carbon chain. It is thought that this deactivation may be water catalysed.

It has now been found that this loss of a sulphur species in the carbonylation reaction may offer advantages in catalysing a subsequent esterification reaction. The sulfur species can be recovered from the esterification reactor and recycled to the carbonylation reactor. Forming an ester provides a product which can more readily be separated from impurities since the problems associated with separating the acid do not apply to the ester and thus separation from impurities can be more readily achieved. Where the desired products may be esters, the desired product may be readily achieved. However, in circumstances where the desired product is the acid, which may be glycolic acid, the separated and hence purified ester can readily be hydrolysed to the acid to provide an acid having the desired level of purity.

Thus, according to the present invention, there is provided a process for the production of glycolic acid or a derivative thereof comprising:
  (a) reacting formaldehyde with carbon monoxide and water in a carbonylation reactor in the presence of a sulfur catalyst, said reactor operating under suitable conditions, such that glycolic acid is formed;
  (b) recovering a first product stream comprising glycolic acid, impurities and a sulfur species in the carbonylation reactor;
  (c) passing the first product stream to an esterification reactor where it is subjected to esterification to form an alkylglycolate and wherein the esterification is catalysed by the sulfur species recovered in the first product stream;
  (d) recovering a second product stream comprising the alkylglycolate, sulfur species and impurities from the esterification reactor;
  (e) separating the sulfur species from the second product stream and recycling it to the carbonylation reactor in step (a) to form a sulphur depleted second product stream;
  (f) separating the alkylglycolate from the sulphur depleted second product stream in a distillation zone; and
  (g) recovering the alkylglycolate and converting the alkylglycolate to glycolic acid.

The conversion of the alkylglycolate to glycolic acid is preferably carried out in a hydrolysis reactor.

DETAILED DESCRIPTION

The formation of the alkylglycolate ester from the glycolic acid in the present invention enables distillation to be carried out to separate the ester from the impurities such that effective separation can be achieved without the drawbacks associated with separating glycolic acid from the impurities. In particular, as the hydroxyl group of the glycolic acid is protected by the esterification, the ability to form dimers or oligomers during distillation is removed.

Since the esterification reaction is catalysed by the sulfur species from the carbonylation reaction in step (a), there is no requirement to add additional catalyst and thus the costs associated therewith are avoided.

Once the esterification reaction has been carried out, the sulfur species can be readily separated from the ester and returned to the carbonylation reactor and as such the use of the sulfur species in the esterification does not represent a loss to the system. Returning the sulfur species to the first carbonylation reactor enables the activity of the catalyst used therein to be maintained or even enhanced.

Since alcohols and carboxylic acids are not present in step (a), the problems associated with by-product formation during the carbonylation step are avoided.

The reaction of the formaldehyde with carbon monoxide and water in step (a) may be carried out by any suitable means.

The water may be present in any suitable amount. For example, the water may be used in an amount from the stoichiometric requirement to a molar ratio of about 4:1 water:formaldehyde.

The water may additionally act as a solvent for the carbonylation reaction. Where water is used as a solvent, it will generally be used in an amount in excess of the ratio detailed above. The water may be provided to the carbonylation reaction zone separately or alternatively it may be supplied in the formaldehyde feed and/or with another solvent.

Alternatively, the water may be present in the amount which is sufficient for the reaction and a separate solvent may be used.

Where a solvent is to be used, it may be the glycolic acid formed in the reaction or it may be a separate solvent. Suitable separate solvents include carboxylic acids or sulphones. Suitable solvents include propionic acid or a sulphone. 2,3,4,5-tetrahydrothiophene-1,1-dioxide may be a suitable sulphone.

The formaldehyde may be supplied as a solution in water or it may be generated in-situ within the carbonylation reaction zone. For example, in one arrangement, paraformaldehyde may be used as a reactant. Paraformaldehyde is a polymer of formaldehyde, which reverts to monomeric formaldehyde in the presence of polar molecules, such as water or alcohol solvents.

The carbon monoxide may be a pure source of carbon monoxide, optionally comprising small quantities of impurities such as one or more of light alkanes, carbon dioxide or hydrogen.

Alternatively, the carbon monoxide source can be a component of a gaseous mixture, for example synthesis gas (syngas), which is a mixture of hydrogen and carbon monoxide.

Any suitable sulfur catalyst may be used. The catalyst may be homogeneous or heterogeneous. Where the catalyst is a heterogeneous catalyst, the sulfur species present in the first product stream may be a sulfur species formed by decomposition of the catalyst.

In one example, the sulfur catalyst may be sulphuric acid.

In an alternative arrangement, an acidic polysiloxane catalyst may be used. Suitable catalysts include those detailed in EP1360222, EP1786850, WO2006/013080, WO2007/090676 and US2010/0290962 the contents of which are incorporated herein by reference. Substituted organopolysiloxane compounds, such as Deloxan ASP 1/9, QuadraSil—SA and Silicycle (SCX-2), and alkyl sulfonic acid polysiloxanes, can be used.

The polysiloxane catalyst may be used alone or in combination with other compounds which may themselves serve as catalysts for the carbonylation reaction or which may be present to assist in stabilizing the polysiloxane catalyst. In one arrangement sulphuric acid may additionally be used as a co-catalyst.

In a further arrangement, the catalyst may be the catalyst system described in WO2016/162663 the contents of which are incorporated herein by reference. In particular, the catalyst system may comprise a homogeneous acid catalyst component and a porous solid component.

Any suitable homogeneous acid catalyst may be used in this system as a component of the catalyst system. Examples include sulfuric acid, triflic acid, sulfonic acids such as methylsulfonic acid, ethanesulfonic acid, p-toluenesulfonic acid, and perfluorooctanesulfonic acid and phosphorous based acids such as phosphonic acid and ethylphosphonic acid. In addition, compositions modified with groups to enhance interaction with the solid component may be used. Examples include trihydroxysilylpropane sulfonic acid, alkyl phosphonic acid, and trihydroxysilylethylsulfonic acid. In another arrangement, formic acid may be used.

Any suitable solid component may be used in the catalyst system provided that it is porous and stable to the reaction environment. Any suitable pore size can be used. In one arrangement it may have a surface area of from about 250 to about 900 m$^2$/g. A surface area of from about 400 to about 750 m$^2$/g or from about 500 to about 600 m$^2$/g may be used. The catalyst system may have a pore volume of from about 0.2 to 1.2 cc/g. In one arrangement, a pore volume of from about 0.5 to about 1.0 cc/g may be used.

Although the solid component may be selected to have some catalytic activity in the absence of the homogeneous component, the combined catalytic effect of the solid component and the homogeneous catalyst surprisingly will be greater than that expected from the components individually.

In one arrangement of this system, the solid component may be unfunctionalised. By "unfunctionalised" we mean that the surface has not been specifically modified to add active catalytic moieties to the surface. In one arrangement the unfunctionalised solid component may have hydroxyl groups located on the surface thereof.

In an alternative arrangement of this system, the solid component may be a functionalised material. By "functionalised" we mean that the material has been modified to have enhanced activity. In one arrangement, the functionalization may be to add alkyl sulfonic acid groups, hydroxyl groups or both alkyl sulfonic acid groups and hydroxyl groups on the surface of the material, in the pores of the solid component or on both the surface and in the pores.

Examples of suitable solid components include silicas, activated carbons, ordered mesoporous carbon, nanoporous carbons, some titanias and zirconias. The silicas may be those from the Johnson Matthey QuadraSil range including SA, TA, AP or MP or QuadraSil PHI available from Sigma Aldrich. Other suitable supports include synthesised ordered mesoporous (or nanoporous) carbons having ordered silica frameworks such as MCM-41, MCM-48, SBA-51, KIT-6, and IITM-56 as templates.

Any suitable amount of homogeneous acid catalyst component may be present in the catalyst system. In one arrangement it may be from: about 10 ppm to about 25 wt %; from about 50 ppm to about 20 wt %; from about 1 wt % to about 15 wt %; or from about 2 wt % to about 10 wt %. The ppm in the solution is ppm weight of acid.

An alternative catalyst system which may be used is the catalyst described in WO2016/162662 the contents of which are incorporated herein by reference. In this arrangement the reaction is carried out in the presence of a silica catalyst, and from about 200 to about 5000 ppm of an alkyl silyl sulfonic acid.

Any suitable silica catalyst may be used in this catalyst system. It may be non-porous or porous. In one arrangement where the catalyst is porous, it may have a surface area of from about 250 to about 500 m$^2$/g and a pore volume of from about 0.2 to 1.2 cc/g. A pore volume of from about 0.5 to about 1.0 cc/g may be used. As supplied to the reactor it may be functionalised or unfunctionalised. Examples of suitable silicas include those from the Johnson Matthey QuadraSil range including SA, TA, AP or MP or QuadraSil PHI available from Sigma Aldrich.

In one arrangement of this system, the solid component may be unfunctionalised. By "unfunctionalised" we mean that the surface has not been specifically modified to add active catalytic moieties to the surface.

In a second arrangement of this system, the solid component may be a functionalised material. By 'functionalised' we mean that the material has been modified to have enhanced activity. In one arrangement, the functionalization may be to add alkyl silyl sulfonic acid groups, hydroxyl groups or both alkyl silyl sulfonic acid groups and hydroxyl groups on the surface of the material.

Any suitable alkyl silyl sulfonic acid may be used in this catalyst system. Suitable acids include trihydroxysilylalkyl sulfonic acid, such as trihydroxysilylpropyl sulfonic acid, or trihydroxysilylethyl sulfonic acid.

The alkyl silyl sulfonic acid may be fresh alkyl silyl sulfonic acid or its addition may be achieved by recycling a portion of the product stream recovered from the reactor which will include alkyl silyl sulfonic acid.

The carbonylation reactor will typically be operated at a temperature in the range of from about 50° C. to about 400° C., for example in the range of from about 100° C. to about 250° C. The reactor will typically be operated at a pressure in the range of from about 1 to about 1000 bara (about 0.1 to about 100 MPa), such as in the range of from 10 to 200 bara (about 0.1 to about 20 MPa).

The carbonylation reaction may be carried out in any suitable manner. In one arrangement it may be conducted in a continuous flow configuration in which carbon monoxide, water, formaldehyde, and optional solvent, either pre-mixed or separately, are introduced to the carbonylation reactor to a fixed bed or slurry reactor containing the acidic polysiloxane catalyst such that the glycolic acid produced can be continuously withdrawn from the reactor. The reaction can take place in single or multiple reactors which may be of different types. The reactors may be arranged in series or in parallel. One or more feedstocks may be added at a single point or sequentially as the reaction progresses.

In one alternative arrangement, the reaction can be conducted batch-wise. This involves suspending and stirring the catalyst in a liquid reaction composition comprising solvent and formaldehyde, with carbon monoxide being fed into the reactor under pressure. The resulting product composition can then be periodically removed from the reactor as the first product stream.

Howsoever formed, the glycolic acid formed will be removed from the carbonylation reactor in the first product stream. This first product stream may then be treated to separate one or more, so-called, 'lights'. 'Lights' are compounds which have a boiling point that is lower than that of the glycolic acid. These lights may include one or more of solvent, unreacted formaldehyde, and unreacted carbon monoxide. Thus, in one arrangement, the first product stream may be passed to a lights separation zone. Other impurities such as alkyl formate, for example methyl formate, and dialkoxymethane, such as dimethoxymethane which is also known as methylal, may be removed by this separation.

The first product stream will additionally also comprise the sulfur species together with one or more, so-called, 'heavies'. These are compounds which have a boiling point that is higher than that of glycolic acid. Any dimers and oligomers of glycolic acid which may form in the carbonylation reactor will be included in these heavies.

As discussed in more detail below, a stream recovered after esterification may be recycled to the carbonylation reactor. Whilst this recycle will generally substantially comprise the sulfur species, it may also include a small quantity of the glycolic acid ester, and/or heavies formed in the carbonylation reactor and their reaction products, if any, which may be formed in the esterification reactor. The ester and any esterification reaction products will then be removed from the carbonylation reactor in the first product stream and form part of the heavies.

The separation of the lights may be carried out by any suitable means, but the lights separation zone will generally be a flash column. Since it is only the light components which are being separated, the temperatures of the lights separation zone can be kept sufficiently low that the disadvantages associated with distilling glycolic acid discussed above do not occur.

The light separation zone will be operated at any suitable temperature which achieves the result. In one arrangement, the light separation zone may be operated at a reboiler temperature of about 140° C. to about 160° C. or at about 150° C. and an overhead temperature of about 75° C. to about 85° C. or at about 80° C. and a pressure of about 1.8 bara to about 2.2 bara or at about 2 bara. At these conditions, significant loss of water in the overheads can be avoided.

The first product stream may be fed to any suitable position in the lights separation zone. Where the lights separation zone comprises a flash column, the first product stream may be fed to the top section of the flash column.

A low boiling point alkanol, such as methanol, may be supplied to the lights separation zone to facilitate separation. The alkanol may be used from battery limit. This may be fed to any suitable position in the lights separation zone. Where the lights separation zone comprises a flash column, the alkanol will generally be fed to the bottom section of the column.

The prime function of this column is to separate unreacted formaldehyde and by-product formic acid from the first product stream. The alkanol, such as methanol, reacts with the formaldehyde to form dialkoxymethane, such as dimethoxymethane, and formic acid reacts with the alkanol, such as methanol, to form alkyl formate, such as methyl formate.

The lights are removed overhead from the lights separation zone and may comprise alkyl formate, alkanol and dialkyloxymethane. Thus where the alkanol is methanol, the overhead from the lights separation zone may comprise mainly methyl formate, methanol and dialkyloxymethane. Whilst the lights separation zone is operated to prevent significant loss of water in the overheads, some water may still be present in the overhead steam. This overhead stream may therefore be passed to a water separation zone, which is generally a water separation column in which water present is separated as a bottom product.

Overheads from the water separation column will generally comprise alkyl formate, alkanol and dialkoxymethane. Thus where the alkanol is methanol the overhead will comprise methyl formate, methanol and dimethoxymethane. The overheads from the water separation column may be fed to a formaldehyde separation column. In this column the alkyl formate, alkanol and dialkoxymethane are separated overhead while alkanol is recovered in the bottoms. The overhead stream will generally be fed as a feed stream to a formaldehyde plant in which the formaldehyde is produced while the bottoms alkanol stream may be used as the alkanol feed to the esterification reactor where alkanol is used for the esterification.

In one alternative arrangement, the overhead stream may be treated such that one or both of the alkyl formate and dialkoxymethane may be separated and recovered.

It is possible that some of the glycolic acid in the lights separation zone may react with the alkanol to form the alkyl ester, for example methyl glycolate. The lights separation zone will therefore generally contain sufficient stages to prevent loss of methyl glycolate overhead.

Where a lights separation zone is present a lights-depleted first product stream is recovered from the light separation zone. This recovery may occur at any suitable position in the lights separation zone but it will generally be taken from at or near the bottom, particularly where the lights separation zone is a flash column.

The first product stream, or where the first product stream is passed through the lights separation zone the lights-depleted first product stream, is passed to an esterification reactor where it is reacted such that a glycolic acid ester is formed.

Generally the stream fed to the esterification reactor will be contacted with an alkanol to effect esterification. Any suitable alkanol may be used for the esterification. Suitable alkanols include methanol, ethanol, propanol or butanol. However, generally methanol will be used.

In one alternative arrangement, the stream fed to the esterification reactor will be contacted with a diol. Any suitable diol may be used for the esterification. One suitable diol is ethylene glycol.

The alkanol or diol provided to the esterification reactor will generally be provided in sufficient amount, in molar terms, to substantially completely esterify the glycolic acid to form alkyl glycolate. In addition sufficient alkanol or diol may be provided to additionally esterify any formic acid which may have been present in the first product stream and which is not removed in the lights separation zone. Further sufficient alkanol or diol will generally be provided to react with any residual formaldehyde which may be present in the feed to the esterification reactor to form dialkoxymethane.

The esterification may be carried out in any suitable reactor. However, generally a plug flow reactor is used although a stirred tank reactor or a reaction column may be used. This esterification is catalysed by the sulfur species recovered in the first product stream. It will be understood that water is also produced in the esterification reaction.

The esterification may be carried out at any suitable temperature and pressure. In one arrangement the reaction will occur at a temperature of from about 90° C. to about 150° C., from about 100° C. to about 140° C., from about 115° C. to about 130° C. or from about 120° C. to about 125° C. The esterification reactor may be operated at a pressure of from about 3 bara to about 7 bara, or from about 4 bara to about 6 bara and may be about 5 bara.

In addition to the desired esterification to form alkyl glycolate, further esterification and trans-esterification reactions may also occur to produce heavier esters.

Since the reactions which occur in the esterification reactor are equilibrium reactions, the second product stream will generally comprise the alkyl glycolate, other esters, glycolic acid and water in addition to the sulfur species and other impurities. The second product stream will also include any unreacted esterification agent. Thus where esterification is carried out with an alkanol, the second product stream will include alkanol. Similarly were the esterification is carried out with a diol, the second product stream will include diol.

The second product stream will then be treated to remove the sulfur species. In one arrangement, the sulfur species may be separated at the same time as the alkyl glycolate is separated. In an alternative arrangement, the sulfur species may be removed before the sulfur species depleted second product stream is treated to recover the alkyl glycolate.

Where the sulfur species is to be separated prior to the recovery of the alkyl glycolate, any suitable separation means may be used. In one arrangement, the sulfur species separation means is an esterification flash drum. The esterification flash drum may be operated at any suitable conditions. In one arrangement, the flash drum will be operated at just above atmospheric pressure. For example, it may be operated at a temperature of from about 140° C. to about 160° C., or from about 145° C. to about 155° C. or at about 150° C. and at a pressure of about 1.5 to about 2.0 bara or at about 1.7 bara to about 1.8 bara.

The sulfur species will generally be recovered from at, or near, the base of the esterification flash drum and recycled to the carbonylation reactor. The stream recovered from the base of the esterification flash drum may comprise some heavy glycolate species.

This sulfur species stream may be passed to a recycle column. The purpose of the recycle column is to prevent alkanol, such as methanol, as alkyl glycolate being recycled to the carbonylation reactor. Where the recycle column is present, water may be added near to the bottom of the recycle column. The purpose of the water is to hydrolyse any alkyl glycolate to alkanol and glycolic acid and to prevent the glycolic acid from oligomerizing and becoming viscous or solid. Any glycolic acid separated in the recycle column may be recovered. An overhead stream from the recycle column, which will comprise mainly alkanol, such as methanol, may be returned to the water separation column where present. A bottoms stream from the recycle column, which will comprise some glycolic acid, water and the sulfur species may be recycled to the reactor in which carbonylation occurs.

The second product stream, or where the sulfur species has been removed the sulfur-depleted second product stream, is passed to the ester distillation column. The distillation may be carried out at any suitable temperature and pressure. However, it will be understood that temperatures which are higher than those which can be used for distillation of glycolic acid may be used. In one arrangement a reactive vacuum distillation at about 0.2 bara to about 0.4 bara, or at about 0.3 bara may be used. In this arrangement the overhead temperature may be about 60° C. to about 65° C. or about 62° C. and the bottoms temperature may be about 130° C. to about 140° C. or about 134° C. to about 135° C. In the ester distillation column the second product stream is separated. The desired alkyl glycolate, such as methyl glycolate, may be recovered as a side draw from at or near the bottom of the ester distillation column. Heavy impurities, which have a higher boiling point than the alkyl glycolate, such as dialkyl diglycolate, will generally be removed from at or near the bottom of the ester distillation columns provided that it is below the position of the side draw to remove the alkyl glycolate. Light impurities, which have a lower boiling point than the alkyl glycolate such as water, alkanol and other light by-products, will generally be removed from at or near the top of the ester distillation column.

Whilst the alkyl glycolate may be recovered as product for use or for subsequent conversion to glycolic acid, it may be converted to the glycolic acid by being passed to a hydrolysis reactor. Any suitable hydrolysis reactor may be used. Generally the alkyl glycolate will be contacted with water to affect hydrolysis. The water will generally be fed as a separate stream. Once the hydrolysis has been carried out the glycolic acid will generally be separated from the water and the alkanol which will be formed.

In one arrangement the hydrolysis reactor may be a reactive distillation column. In this arrangement, the glycolic acid may be recovered as a bottoms product and water and alkanol may be removed as a lights overhead stream. The lights overhead stream may be recycled to upstream processing.

Where a reactive distillation column is used for the hydrolysis, it may be operated at any suitable conditions. In one arrangement the column will be operated at a pressure of about 1.0 bara to about 1.5 bara, or at about 1.2 bara. In this arrangement the overhead temperature may be about 75° C. to about 85° C. or about 79° C. to about 80° C. and the bottoms temperature may be about 130° C. to about 140° C. or about 134° C. to about 135° C.

A catalyst may be required where the hydrolysis is carried out in a reactive distillation column. In one arrangement the glycolic acid may act as catalyst. However, an additional catalyst may be used. Where a catalyst is used it may be a homogeneous catalyst such as sulphuric acid or it may be a suitable solid catalyst which will be located on the trays within the column. If a homogeneous catalyst is used it will need to be removed from the glycolic acid product.

In one alternative arrangement, the hydrolysis reactor may be carried out by ion exchange reactor. Any suitable apparatus or ion exchange material may be used.

The glycolic acid may have the desired level of purity of about 70% by weight. Optionally, the glycolic acid recovered from the hydrolysis reactor may be further purified for example by being passed through an ion exchange purification system to remove any residual sulphuric acid. Where the hydrolysis is carried out by ion exchange this further purification step may not be required.

The present invention will now be described by way of example with reference to the accompanying drawing, in which.

It will be understood by those skilled in the art that the figures are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

The present invention will be described with particular reference to the formation of a methyl glycolate. However, it will be understood that other alkyl esters may be used.

Figure 1:
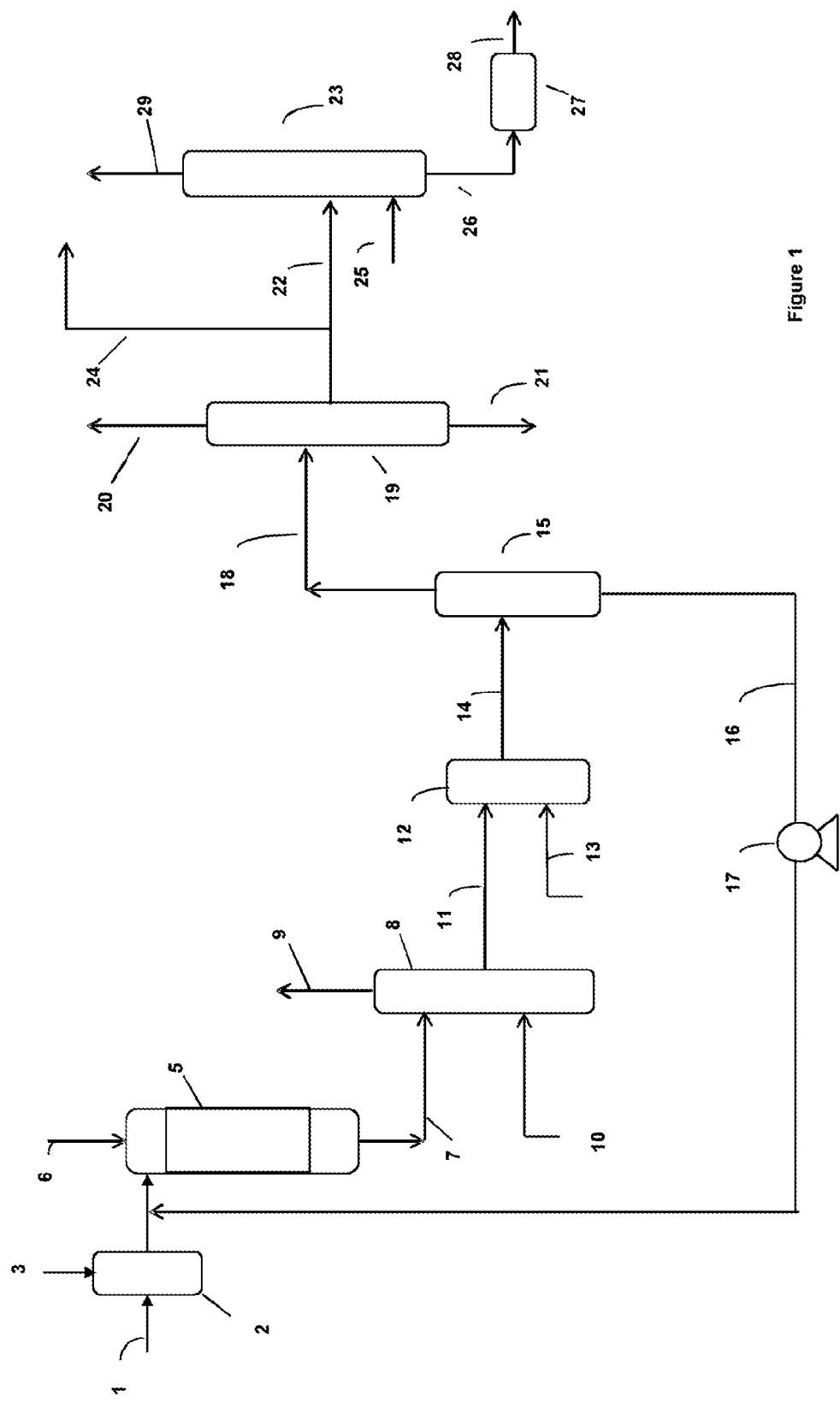
FIG. 1 is a schematic illustration of the process of the present invention.

As illustrated in FIG. 1, formaldehyde, such as 55 wt % aqueous formaldehyde, is passed in line 1 to a mixing tank 2 where it is mixed with the sulfur catalyst added in line 3. The mixed formaldehyde is passed in line 4 to the carbonylation reactor 5 where it is reacted with carbon monoxide which is supplied to the reactor in line 6.

The first product stream is recovered in line 7. This stream will comprise glycolic acid, sulfur species and impurities which may be selected from methyl formate, formic acid, methylal, methanol and formaldehyde. It is passed to a lights separation zone 8 where lights which may include methyl formate, methylal, methanol and formaldehyde will be removed in line 9. Methanol may be added in line 10 to facilitate separation.

A stream including the glycolic acid is taken at or near the bottom in line 11. This will generally be removed below the position of the methanol feed. The stream is then passed to the esterification reactor 12 where it is contacted with methanol added in line 13. The esterification reactor may be a plug flow reactor. A second product stream comprising the methyl glycolate, the sulfur species and impurities is recovered from the reactor in line 14 and passed to the esterification flash drum 15 where the sulfur species are separated.

The sulfur species is recovered in line 16. The pump 17 facilitates the return of the sulfur species and any heavy recycle may be returned to the carbonylation reactor 5. The heavy recycle may be fed directly to the reactor or it may be fed into line 4.

The methyl glycolate is recovered in second product stream in line 18. This stream will also include water, and impurities. This stream is fed to the ester separation column 19 where light impurities such as water, methanol and light by-products are removed as column overheads 20 and heavy impurities such as dimethyl diglycolate are recovered in line 21.

The methyl glycolate may be recovered as a side draw in line 22. This will generally be taken below the point at which feed is added. Where the desired product is glycolic acid, the recovered methyl glycolate may be passed to hydrolysis reactor 23. Methyl glycolate may optionally be taken as an off-take in line 24. Water is supplied to the hydrolysis reactor 23 in line 25. It may also be necessary to add catalyst to the hydrolysis reactor 23. Where this is a heterogeneous catalyst it will be provided on trays within the reactor 23. Where it is a homogeneous catalyst it may be added into line 22 before the methyl glycolate is supplied to the hydrolysis reactor. The glycolic acid is removed from the hydrolysis reactor 23 in line 26 where it may optionally be passed through an ion exchange purifier 27 before being recovered in line 28. Methanol and water is recovered from the hydrolysis reactor as an overhead in line 29. In one alternative, the hydrolysis reactor is replaced with an ion exchange system.

Figure 2:
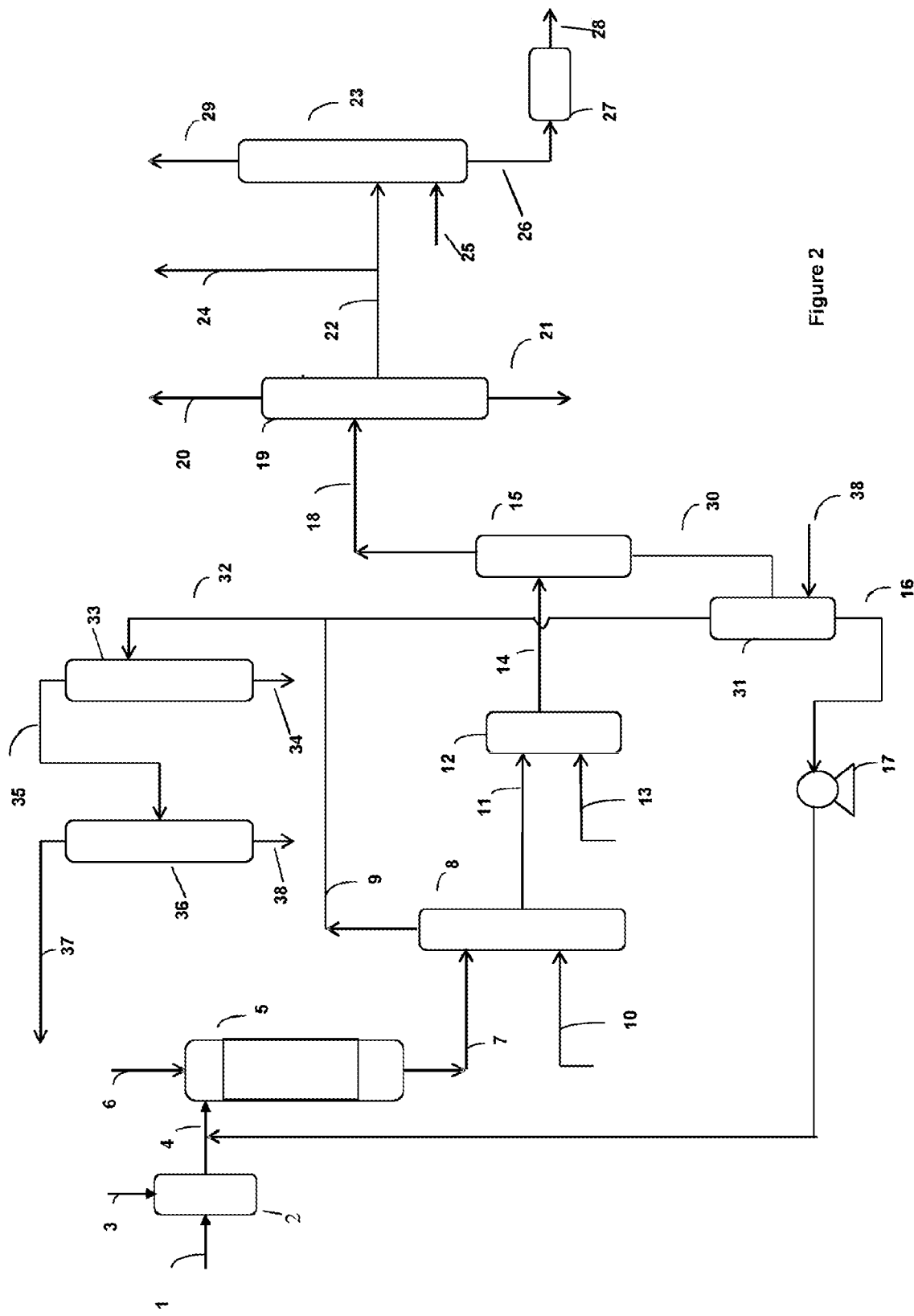
FIG. 2 is a schematic illustration of an alternative arrangement of the present invention.

An alternative arrangement is illustrated in FIG. 2. Much of this arrangement is the same as in FIG. 1. In this arrangement, the stream recovered from the bottom of the esterification flash drum 15 is passed in line 30 to a recycle column 31. Water may be added to the recycle column in line 38. The bottom stream from the recycle column 31 is fed in line 16 to the carbonylation reactor 5.

The overheads from the recycle column 31 are passed in line 32 to the water separation column 33. The overhead stream 9 from the lights separation zone 8 may also be passed to the water separation column 33. It may be supplied separately or may be combined with stream 32 before being passed to the water separation column 33. Water is removed from the bottom of the water separation column in line 34.

The overheads from the water separation column are passed in line 35 to the formaldehyde separation column 36. Methanol is recovered in line 38. The overhead will generally be recovered in line 37 and sent to the formaldehyde plant The present invention will now be described with reference to the following example.

Example 1

The simulation platform Aspen Plus V8.8 was used to simulate the esterification and hydrolysis columns. The physical properties used in the simulation were sourced using a combination of Aspen plus databanks, and property estimation methods The process conditions for the ester separation and hydrolysis columns which are reactive distillation columns, used the following conditions:

|  | Ester Separation Column | Hydrolysis Column |
| --- | --- | --- |
| Column Top P (bara) | 0.3 | 1.2 |
| Column Top T (° C.) | 61.9 | 79.2 |
| Column Base T (° C.) | 133.8 | 134.0 |

The reactions included in the simulation are primarily esterification of glycolic acid (GA), methoxyacetic acid (MAA), diglycolic acid (DGA) with methanol, plus hydrolysis of the resulting esters, namely methyl glycolate (MG), methylmethoxyacetate (MMA), methyl diglycolate (M-DG) and dimethyl digylcolate (M-DG-M). The esterification reaction was catalysed by $H_2SO_4$.

The stream compositions derived in the simulation are set out in the Table below. The stream numbers correspond to the streams indicated in FIG. 1.

| Composition wt % | 18 | 20 | 21 | 22 | Catalyst Supplied to line 22 | 25 | 29 | 26 | 28 |
| --- | --- | --- | --- | --- | --- | --- | --- | --- | --- |
| Lights | 0.271 | 0.492 | 0 | 0 | 0 | 0 | 0 | 0 | 0 |
| Water | 25.415 | 46.626 | 0 | 0 | 7.0 | 100.0 | 15.508 | 25.005 | 25.161 |
| GA | 0.926 | 0 | 13.25 | 0.507 | 0 | 0 | 0 | 73.999 | 74.46 |
| MeOH | 25.056 | 46.013 | 0 | 0 | 0 | 0 | 84.387 | 0.007 | 0.007 |
| DGA | 0 | 0 | 0 | 0 | 0 | 0 | 0 | 0.208 | 0.21 |
| MG | 43.921 | 0.1 | 76.852 | 99.077 | 0 | 0 | 0.104 | 0.052 | 0.052 |
| MAA | 0.165 | 0 | 2.276 | 0.095 | 0 | 0 | 0 | 0.109 | 0.11 |
| MMA | 3.703 | 6.77 | 0.001 | 0.034 | 0 | 0 | 0.001 | 0 | 0 |
| M-DG | 0.006 | 0 | 0.083 | 0.003 | 0 | 0 | 0 | 0 | 0 |
| M-DG-M | 0.535 | 0 | 7.509 | 0.283 | 0 | 0 | 0 | 0 | 0 |
| Sulphuric acid | 0.002 | 0 | 0.028 | 0.001 | 93.0 | 0 | 0 | 0.618 | 0 |
| Mass Flow (kg/hr) | 6501 | 3542 | 365 | 2594 | 20 | 1419 | 1086 | 2947 | 2928 |

The lights constitute of formaldehyde, formic acid, methyl formate and methylal.

In the example presented here, the rate of methyl glycolate hydrolysis is enhanced by the addition of a homogeneous catalyst ($H_2SO_4$) in the feed to the hydrolysis reactor. This could also be achieved via heterogeneous catalysis and/or by operating the column at a higher pressure.

It will be understood that catalyst is required in a number of parts in the flowsheet. Where a homogeneous catalyst, such as sulphuric acid, is used, the catalyst will pass through the flowsheet and so the same catalyst can be used. However, a separate catalyst will generally be required for the final hydrolysis of the product.

What is claimed:

1. A process for the production of glycolic acid or a derivative thereof comprising:
    (a) reacting formaldehyde with carbon monoxide and water in a carbonylation reactor in the presence of a sulfur catalyst, said reactor operating under suitable conditions, such that glycolic acid is formed;
    (b) recovering a first product stream comprising glycolic acid, impurities and a sulfur species in the carbonylation reactor;
    (c) passing the first product stream to an esterification reactor where it is subjected to esterification to form an alkylglycolate and wherein the esterification is catalysed by the sulfur species recovered in the first product stream;
    (d) recovering a second product stream comprising the alkylglycolate, sulfur species and impurities from the esterification reactor;
    (e) separating the sulfur species and the alkylglycolate from the second product stream,
    (f) recycling the sulfur species to the carbonylation reactor in step (a) and
    (g) converting the alkylglycolate to glycolic acid.

2. The process according to claim 1 wherein the molar ratio of water formaldehyde is about 4:1.

3. The process according to claim 1 wherein a solvent is used in the carbonylation reactor.

4. The process according to claim 3 wherein the solvent is propionic acid or a sulphone.

5. The process according to claim 4 wherein the solvent is 2,3,4,5-tetrahydrothiophene-1,1-dioxide.

6. The process according to claim 1 wherein the carbonylation reactor is operated at a temperature in the range of from about 50° C. to about 400° C. and at a pressure in the range of from about 1 to about 1000 bara (about 0.1 to about 100 MPa).

7. The process according to claim 1 wherein the first product stream is passed to a lights separation zone.

8. The process according to claim 7 wherein the light separation zone is operated at a reboiler temperature of about 140° C. to about 160° C., an overhead temperature of about 75° C. to about 85° C., and a pressure of about 1.8 bara to about 2.2 bara.

9. The process according to claim 7 wherein a low boiling point alkanol is supplied to the lights separation zone.

10. The process according to claim 7 wherein an overhead recovered from the lights separation zone is passed to a water separation zone.

11. The process according to claim 10 wherein an overhead from the water separation zone is fed to a formaldehyde separation column.

12. The process according to claim 1 wherein the esterification is carried out at a temperature of from about 90° C. to about 150° C.

13. The process according to claim 1 wherein the esterification reactor is operated at a pressure of from about 3 bara to about 7 bara.

14. The process according to claim 1 wherein the sulfur species is removed prior to the alkylglycolate.

15. The process according to claim 1 wherein the sulfur species is separated in an esterification flash drum and recovered in a sulfur species stream.

16. The process according to claim 15 wherein the esterification flash drum is operated at a temperature of from about 140° C. to about 160° C., and at a pressure of about 1.5 to about 2.0 bara.

17. The process according to claim 15 wherein the sulfur species is recycled to the carbonylation reactor.

18. The process according to claim 15 wherein the sulfur species stream is passed to a recycle column.

19. The process according to claim 18 wherein water is added to the bottom of the recycle column.

20. The process according to claim 1 wherein the alkylglycolate is removed in an ester distillation column.

21. The process according to claim 20 wherein the ester distillation column is carried out at a pressure of about 0.2 bara to about 0.4 bara.

22. The process according to claim 20 wherein an overhead temperature in the ester distillation column is about 60° C. to about 65° C. and a bottom temperature is about 130° C. to about 140° C.

23. The process according to claim 1 wherein the alkylglycolate is converted to glycolic acid in a hydrolysis reactor.

24. The process according to claim 23 wherein the hydrolysis reactor is a reactive distillation column.

25. The process according to claim 23 wherein a catalyst is added to the reactive distillation column.

26. The process according to claim 1 wherein the alkylglycolate is converted to glycolic acid by ion exchange.

* * * * *